United States Patent
Yateem et al.

(10) Patent No.: US 11,118,452 B1
(45) Date of Patent: Sep. 14, 2021

(54) MULTIPHASE FLOWMETERS AND RELATED METHODS FOR OIL AND GAS APPLICATIONS

(71) Applicant: Saudi Arabian Oil Company, Dhahran (SA)

(72) Inventors: Karam Yateem, Qatif (SA); AbdulRahman Al-Ghamdi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/865,850

(22) Filed: May 4, 2020

(51) Int. Cl.
*E21B 49/08* (2006.01)
*E21B 47/12* (2012.01)
*G01F 1/56* (2006.01)

(52) U.S. Cl.
CPC .............. *E21B 49/08* (2013.01); *E21B 47/12* (2013.01); *G01F 1/56* (2013.01)

(58) Field of Classification Search
CPC . E21B 49/08; E21B 47/12; G01F 1/56; G01F 1/06; G01F 1/662; G01F 15/00; G01F 15/18; G01F 11/029
See application file for complete search history.

(56) References Cited

U.S. PATENT DOCUMENTS

| | | |
|---|---|---|
| 6,658,944 B2 | 12/2003 | Melnikov et al. |
| 7,827,869 B2 | 11/2010 | Kitami et al. |
| 7,942,065 B2 | 5/2011 | Xie |
| 9,159,166 B2 | 10/2015 | Finn et al. |
| 9,671,793 B2 | 6/2017 | Atherton |
| 10,060,774 B1 * | 8/2018 | Bartlett .................. G01F 15/00 |
| 10,309,910 B2 | 6/2019 | Sharma et al. |
| 2010/0176161 A1 * | 7/2010 | Conner ................ G01F 11/029 |
| | | 222/389 |
| 2019/0226893 A1 * | 7/2019 | Kuhlemann ............ G01F 15/18 |

* cited by examiner

*Primary Examiner* — Regis J Betsch
*Assistant Examiner* — Kaleria Knox
(74) *Attorney, Agent, or Firm* — Fish & Richardson P.C.

(57) ABSTRACT

A flowmeter includes a fluid collection chamber for receiving a fluid flow, an adjustable collection tube configured to receive a portion of the fluid flow to generate one or more first measured parameters of multiple measured parameters of the fluid flow, a sampling chamber configured to measure samples of the fluid flow to generate one or more second measured parameters of the multiple measured parameters of the fluid flow, and a control module in signal communication with the adjustable collection tube and the sampling chamber and including one or more processors by which the control module automatically performs certain operations. Such operations include determining multiple output parameters of the fluid flow based on the multiple measured parameters and multiple input parameters. Such operations further include controlling a size of the adjustable collection tube based on a property of the fluid flow.

20 Claims, 5 Drawing Sheets

MULTIPHASE FLOWMETERS AND RELATED METHODS FOR OIL AND GAS APPLICATIONS

TECHNICAL FIELD

This disclosure relates to multiphase flowmeters and related methods of analyzing a fluid produced by a well.

BACKGROUND

Flow measurement devices are widely used in oil and gas applications for measuring various parameters of effluent flowing from a well. The effluent is typically in the form of a multiphase fluid that includes oil, gas, and water, and the parameters that are measured may include a well potential (for example, a flow rate of the effluent) and other aspects of the effluent. Continuously and accurately measuring the parameters of the effluent can be challenging for several reasons. For example, a flow measurement device may be sized or otherwise configured to handle well potentials or other effluent properties only within certain ranges, reservoir characteristics only of certain types, and power requirements within certain ranges. Additionally, any of these aspects may vary during operation. Therefore, inadequate determination or monitoring of these variable aspects can lead to suboptimal performance of a flow measurement device at a well and various field interventions that increase operational costs and downtime of associated equipment at the well.

SUMMARY

This disclosure relates to a multiphase flowmeter (MPFM) that is designed to determine various parameters of a multiphase fluid flow of oil, gas, and water produced by a well in real time. The MPFM includes a fluid collection chamber that receives a fluid volume from the multiphase flow, an adjustable sampling chamber that receives fluid samples from the fluid collection chamber through multiple openings, multiple fluid processing devices that measure aspects of the fluid volume, an output line that receives the fluid volume from the adjustable sampling chamber, and a control module (for example, an electronics module) that controls multiple operations of the MPFM. Example fluid processing devices include pressure, differential pressure, and temperature sensors and transmitters, a radioactive measurement system, and capacitance and inductance sensors. A physical input device (for example, a button) may also be associated with the MPFM as a back-up measure for alternatively controlling the MPFM 100 as part of a manual intervention in case of any problems related to automated functioning of the MPFM. The multiphase flow is analyzed when required at the imbedded sampling chamber. The sampling chamber is normally closed, but opens and activates for use when a sample is required for analysis. The sampling chamber remains open until filled with fluid and remains activated until the fluid is analyzed.

The control module receives input data related to the well and determines, simulates, and forecasts output parameters of the multiphase fluid flow from the input data and from measured parameters of the fluid flow. The control module sends signals carrying data corresponding to the output parameters to a surface monitoring unit and generates warnings (for example, alarms or notifications) in associated with any significant divergence between actual output parameters and expected output parameters. The control module is also designed to control positions of walls of the adjustable sampling chamber to change the volume capacity of the adjustable sampling chamber based on characteristics of the well producing the multiphase fluid flow. The control module is further capable of updating stored empirical relationships between the input data and measured parameters of the fluid volume for determining accurate output parameters of the multiphase flow and carrying out auto-calibration events. According to these and other features of the control module, the MPFM is a smart, robust device that is adaptable to variable conditions of multiple wells for accurate characterization of a multiphase fluid flow.

In one aspect, a flowmeter includes a fluid collection chamber for receiving a fluid flow, an adjustable collection tube configured to receive a portion of the fluid flow to generate one or more first measured parameters of multiple measured parameters of the fluid flow, a sampling chamber configured to measure samples of the fluid flow to generate one or more second measured parameters of the multiple measured parameters of the fluid flow, and a control module in signal communication with the adjustable collection tube and the sampling chamber and including one or more processors by which the control module automatically performs certain operations. Such operations include determining multiple output parameters of the fluid flow based on the multiple measured parameters and multiple input parameters. Such operations further include controlling a size of the adjustable collection tube based on a property of the fluid flow.

Embodiments may provide one or more of the following features.

In some embodiments, the property includes a bulk flow rate, and the operations further include causing a size of the adjustable collection tube to increase when the bulk flow rate increases and causing a size of the adjustable collection tube to decrease when the bulk flow rate decreases.

In some embodiments, the sampling chamber is configured to sample the fluid flow continuously and to send signals corresponding to the one or more second measured parameters to the control module in real time.

In some embodiments, the operations further include receiving the multiple input parameters, the multiple input parameters being related to the fluid flow and to a well that produces the fluid flow.

In some embodiments, the operations further include updating one or more of the multiple input parameters based on one or more of the multiple output parameters.

In some embodiments, the operations further include sending the multiple output parameters to a surface monitoring unit.

In some embodiments, the operations further include generating an alarm or a notification when a difference between a value of an output parameter and an expected value exceeds a threshold value.

In some embodiments, the fluid flow includes multiple phases, and the multiple output parameters include bulk properties of the fluid flow and phase properties of the multiple phases.

In some embodiments, the operations further include auto-calibrating the flowmeter using one or more of the multiple measured parameters and validating one or more of the multiple output parameters based on one or more of the multiple measured parameters.

In some embodiments, the flowmeter further includes one or more fluid processing devices configured to measure parameters of the fluid flow.

In another aspect, a method of analyzing a fluid produced by a well includes receiving the fluid flow within a fluid collection chamber, generating one or more first measured parameters of multiple measured parameters of the fluid flow at an adjustable collection tube in fluid communication with the fluid collection chamber, generating one or more second measured parameters of the multiple measured parameters at a sampling chamber in fluid communication with the fluid collection chamber, determining multiple output parameters of the fluid flow based on the multiple measured parameters and multiple input parameters at one or more processors of a control module in signal communication with the adjustable collection tube and the sampling chamber, and controlling a size of the adjustable collection tube based on a property of the fluid flow at the one or more processors of the control module.

Embodiments may provide one or more of the following features.

In some embodiments, the property includes a bulk flow rate, and the method further includes increasing a size of the adjustable collection tube when the bulk flow rate increases and decreasing the size of the adjustable collection tube when the bulk flow rate decreases.

In some embodiments, the sampling chamber is configured to sample the fluid flow continuously and to send signals corresponding to the one or more second measured parameters to the control module in real time.

In some embodiments, the method further includes receiving the multiple input parameters at the control module, the multiple input parameters being related to the fluid flow and to the well.

In some embodiments, the method further includes updating one or more of the multiple input parameters based on one or more of the multiple output parameters at the control module.

In some embodiments, the method further includes sending the multiple output parameters from the control module to a surface monitoring unit.

In some embodiments, the method further includes generating an alarm or a notification when a difference between a value of an output parameter and an expected value exceeds a threshold value at the control module.

In some embodiments, the fluid flow includes multiple phases, and the multiple output parameters include bulk properties of the fluid flow and phase properties of the multiple phases.

In some embodiments, the method further includes auto-calibrating the flowmeter at the control module using one or more of the multiple measured parameters and validating one or more of the multiple output parameters at the control module based on one or more of the multiple measured parameters.

In some embodiments, the method further includes generating one or more third measured parameters of the multiple measured parameters at one or more fluid processing devices in fluid communication with the fluid collection chamber.

The details of one or more embodiments are set forth in the accompanying drawings and description. Other features, aspects, and advantages of the embodiments will become apparent from the description, drawings, and claims.

DETAILED DESCRIPTION

Figure 1:
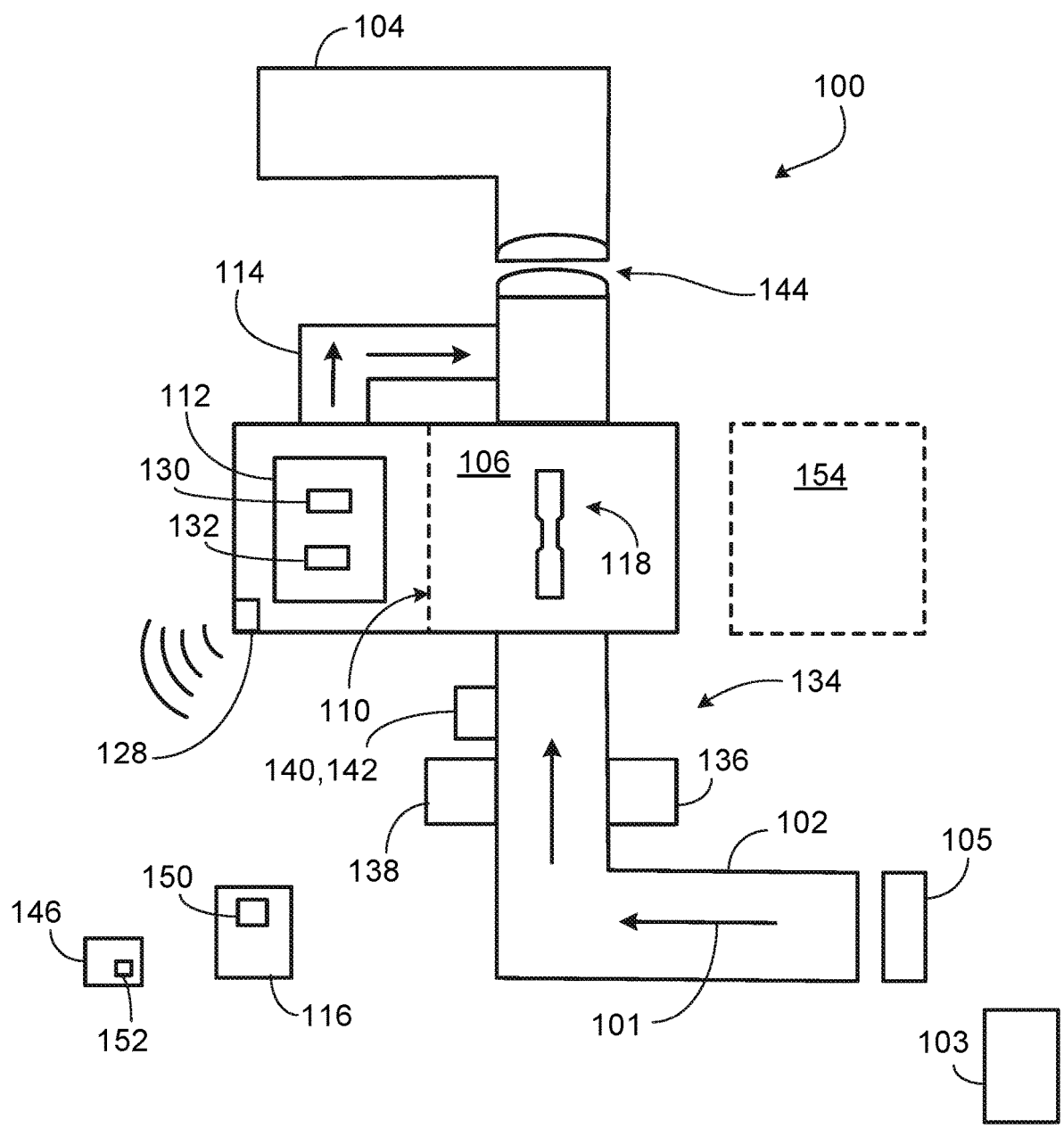
FIG. 1 is a schematic illustration of a multiphase flowmeter.

FIG. 1 schematically illustrates a multiphase flowmeter (MPFM) 100 that is designed to determine various parameters of an effluent produced by a well 103 in real time. The effluent is a multiphase, commingled fluid flow 101 of oil, gas, and water. The MPFM 100 receives the fluid flow 101 from an incoming flow line 102 (for example, a well flow line) that is connected to the well 103 and ultimately delivers the fluid flow 101 to an outgoing flow line 104 (for example, a test line) that is connected to a production line 105. The MPFM 100 may be positioned within proximity to one or more (for example, one to forty) outgoing flow lines of one or more respective wells for selectively servicing any one of the one or more wells at a given time. Depending on whether the one or more wells are disposed in an onshore environment or an offshore environment, the MPFM 100 may be located anywhere from about 10 meters (m) to about 20 m from each of the one or more wells to be serviced.

The MPFM 100 includes a fluid collection chamber 106 that receives the fluid flow 101 from the incoming flow line 102, a sampling chamber 108 that receives the fluid flow 101 from the fluid collection chamber 106 through multiple openings 110, multiple fluid processing devices 112 that measure aspects of the fluid flow 101 within the sampling chamber 108, an exit line 114 that delivers the fluid flow 101 from the sampling chamber 108 to the outgoing flow line 104, and a control module 116 that controls multiple operations of the MPFM 100. The control module 116 includes one or more processors 150 by which software algorithms are executed for controlling the operations. An manual input device 152 (for example, a button) may also be installed at a surface monitoring unit 148 or at another location that allows for manual control of the MPFM 100.

Figure 2:
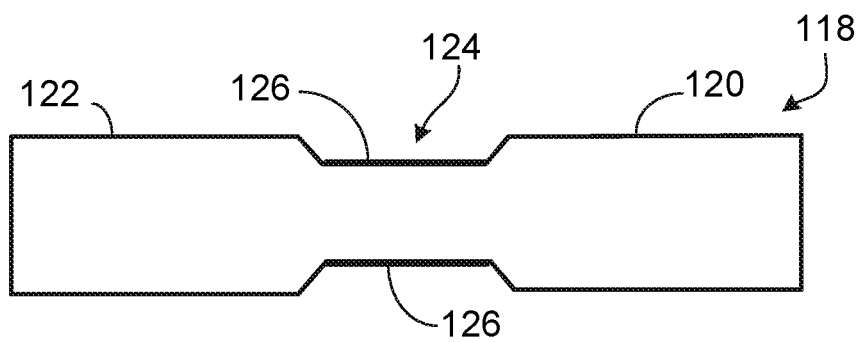
FIG. 2 is a side view of a collection tube of the multiphase flowmeter of FIG. 1.

Referring to FIGS. 1 and 2, the MPFM 100 also includes a collection tube 118 that is adjustable in size for receiving a variable fluid volume. The collection tube 118 is disposed within the fluid collection chamber 106 and generally operates according to the principles of the Venturi effect, which is a reduction in fluid pressure that results when a fluid flows through a pipe section of reduced diameter. The collection tube 118 includes an inlet channel 120, an outlet channel 122, and a narrowed intermediate channel 124 disposed between the inlet and outlet channels 120, 122. The control module 116 can determine a bulk flow rate of the fluid flow 101 from a differential fluid pressure measured across the intermediate channel 124 and various input parameters received at the control module 116, such as fluid properties of the fluid flow 101, as will be discussed in more detail below.

As indicated by the double-headed arrows in FIG. 2, positions of walls 126 of the intermediate channel 124 are automatically adjustable (for example, hydraulically adjustable) in real time based on a positive feedback loop for varying a fluid volume that is collected within the intermediate channel 124 based on a flow rate of the fluid flow 101 (for example, the well potential of the well 103). In other cases, the walls 126 may be adjusted based on other effluent properties of the fluid flow 101 or differential pressure readings. Based on control signals transmitted by the control module 116, the walls 126 may be moved outward to expand the volume of the intermediate channel 124 when the flow rate of the fluid flow 101 is relatively high or moved inward to decrease the volume of the intermediate channel 124 when the flow rate of the fluid flow 101 is relative low.

In particular, a volume capacity of the intermediate channel 124 can increase or decrease to ensure that readings are within an acceptable parameter envelope for sufficient accuracy and validity. In some examples, the volume capacity can change when the fluid flow 101 does not exert enough force to cause any differential pressure reading associated with the collection tube 118. In some examples, movement of the walls 126 may be automatically controlled according to control logic. In some examples, movement of the walls 126 may additionally or alternatively be controlled manually or automatically using the button 152 for manually moving the walls 126. For example, the control module 116 can record the differential pressure of the fluid flow 101 entering the collection tube 118. If the differential pressure is outside of an acceptable operating range, then the control module 116 will estimate a recommended volume capacity of the intermediate channel 124 based on control logic or advanced algorithms and will cause the walls 126 to adjust to ensure that differential pressure readings are within the acceptable operating range, or signal manual control of the walls 126 at button 152. Alternatively, maintenance personnel can open an upper flange 144 or the fluid collection chamber 106 to replace the collection tube 118 with another collection tube of an appropriate size based on the flow rate of the fluid flow 101 and a historical performance of the well. In such cases, the control module 116 will automatically examine the updated conditions and verify functionality before further operations can continue.

Referring to FIG. 1, the sampling chamber 108 is designed for measuring various other properties of the fluid flow 101 that, together with the bulk flow rate and various input parameters, can be used by the control module 116 to determine multiple output parameters related to the fluid flow 101 continuously in real time. The openings 110 are normally closed and will open at the time of sample collection. The sampling chamber 108 includes the fluid processing devices 112 and a signaling device 128 (for example, a transceiver) that receives signals from the fluid processing devices 112 and transmits corresponding signals 160 to the control module 116 in real time. The fluid processing devices 112 may include a centrifuge 130 and a densitometer 132 that respectively measure a liquid fraction and a density of each phase of the fluid flow 101. The liquid fractions may include a water cut (WC) (for example, a liquid fraction of water within the fluid flow 101) and a gas oil ratio (GOR) (for example, a ratio of gas to oil within the fluid flow 101). The centrifuge 130 and the densitometer 132 send signals corresponding to the liquid fractions and the densities via the signaling device 128 to the control module 116 for determining mass attenuation coefficients of the phases of the fluid flow 100.

The MPFM 100 also includes additional fluid processing devices. For example, the MPFM 100 includes a radioactive measurement system 134 that determines a bulk density (for example, a mixture density) of the fluid flow 101 in real time. The radioactive measurement system 134 includes a radioactive source 136 that emits radiation into the fluid flow 101 within the sample chamber 108 and a gamma ray detector 138 that receives any radiation that passes through the fluid flow 101. The detector 138 transmits signals corresponding to the received radiation (for example, based on the number of pulses received into the detector 138) to the control module 116 continuously in real time, and the control module 116 determines the bulk density of the fluid flow 101 based on the signals from the detector 138 and various input parameters received at the control module 116. The MPFM 100 also includes a pressure sensor 140 and a temperature sensor 142 that respectively measure a bulk pressure and a bulk temperature of the fluid flow 101 and transmit corresponding signals to the control module 116 continuously in real time.

The control module 116 receives multiple input parameters (for example, initial data) related to the well 103 from one or more databases in an automated manner and measurement data related to the fluid flow 101 from the signaling device 128 of the sampling chamber 108 to determine the bulk and phase flow rates, bulk and phase densities, and liquid fractions, as discussed above. The control module 116 is further capable of determining (for example, calculating) and performing virtual metering (for example, simulating and forecasting the behavior of the MPFM 100) to determine multiple other output parameters related to the fluid flow 101 from the input parameters and the measurement data. The control module 116 sends signals carrying data corresponding to the output parameters to a surface monitoring unit 146 (for example, a personnel computer). As discussed above, the control module 116 is also designed to control the positions of the walls 126 of the collection tube 118 based on the flow rate of the fluid flow 101. Additionally, the control module 116 is operable to generate alarms and notifications and send such warnings to the surface monitoring unit 146 when a difference between an actual output parameter and an expected output parameter (for example, a forecasted, simulated, or otherwise expected value) differs by more than a threshold tolerance.

The input parameters received by the control module 116 include various computational flow models and empirical data (for example, including historical data). Example models that may be utilized include the industry standard black oil model, a customized fluid identification model, and a liquid reference model. The empirical data may include various characteristics of the well (for example, an expected pressure-volume-temperature (PVT) profile and a reservoir bubble point pressure), operating temperature and pressure ranges of the MPFM 100, expected parameters of the fluid flow 101 (for example, water density, water salinity, reservoir GOR), and various hydrocarbon contents of the fluid flow 101. The control module 116 is further operable to perform real time test validation with respect to models of the well potential, historical performance, and virtual metering. Physical wellhead sampling can be utilized to compare and validate a performance of the MPFM 100 based on measurements of the water cut of the fluid flow 101.

The control module 116 is capable of updating stored empirical relationships of the input data (for example, the PVT profile and the well potential) based on measured aspects of the fluid flow 101 from sampling chamber 108 for maintaining the accuracy of output parameters related to the fluid flow 101. The PVT profile may be a key aspect of one or more of the input models and can directly affect validity of the output parameter results. For example, one or both of the PVT and a water salinity may be of particular significance in water injection fields or in offshore environments where the MPFM 100 is connected to a large number of wells with different properties that are variable.

Frequent, automated sampling at the sampling chamber 108 and sample analysis at the control module 116, along with updating the input parameters in relation to proprieties of the fluid flow 101, will directly affect measurements at the MPFM 100. This is especially important in cases where expected results differ significantly from results measured at the MPFM 100. As mentioned above, the control module 116 can analyze any potential errors and generate an alarm or notification if a physical intervention is required. Otherwise, a soft action may be performed or considered for verifying the accuracy or healthiness of the MPFM 100, such as taking a sample, measuring properties of the sample, and recalibrating any input models with the new properties. Accordingly, to maintain the accuracy of measured parameters and output parameters determined based on the measured parameters, the fluid flow 101 is delivered to the MPFM 100 through the incoming flow line 102. The fluid flow 101 is sampled automatically within the sample chamber 108, and signals are sent to the control module 116 for analysis and adjustment of the PVT profile as necessary.

Figure 3:
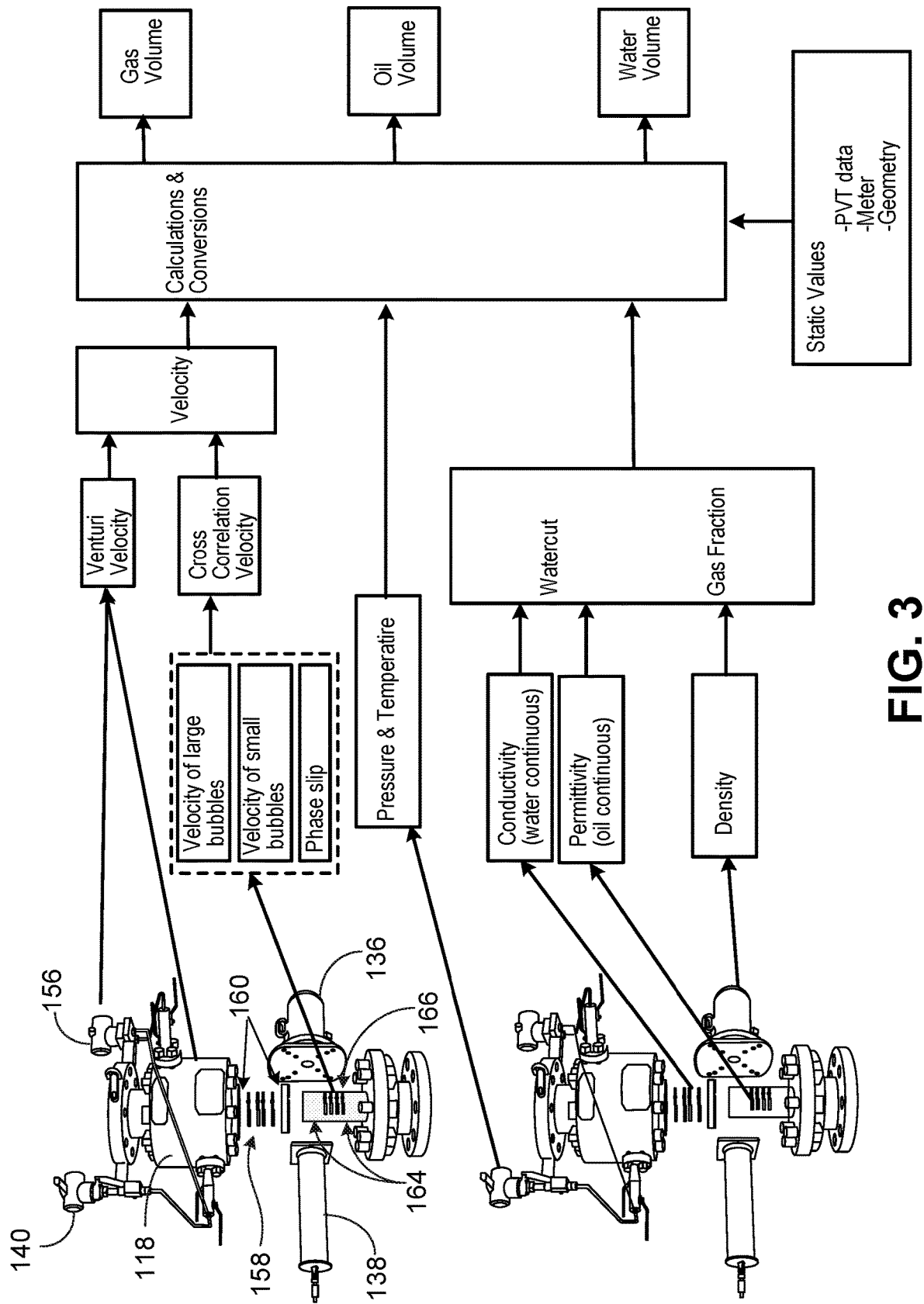
FIG. 3 is an exploded perspective view of various components of the multiphase flow meter of FIG. 1 in association with various flow properties generated by the components.

FIG. 3 provides an exploded view of various components of the MPFM 100 and indicates various parameters that may be generated via the components. (The components are illustrated in duplication for clarity in pointing out the various parameters.) In addition to the components already described above, the MPFM 100 includes a differential pressure transmitter 156 for measuring the differential pressure across the collection tube 118, an inductance sensor including inductive electrodes 158 and inductive coils 160, and a capacitance sensor including large capacitive electrodes 164 and small capacitive electrodes 166. The capacitance sensor measures fractions of oil, water, and gas of the fluid flow 101. The capacitance sensor is also used for measuring a capacitance in the pipe and calculating a permittivity of the fluid flow 101. The capacitance sensor is mainly utilized in an oil-continuous mode to calculate the water cut. The capacitance sensor is not suitable in a water-continuous mode. For this reason, the conductivity of the fluid flow 101 is measured by the inductive sensor during a water-continuous mode.

To set up the MPFM 100, the MPFM 100 can be installed at the incoming and outgoing flow lines 102, 104, and an integrity check can then be performed on the MPFM 100. The integrity ensures that no leak is present and that all individual components are functioning properly according to manufacturing specifications. The above-discussed input parameters are then received at the control module 116. The MPFM 100 is designed to auto-calibrate its own operation at this stage of commissioning. The control module 116 is designed to send out an alarm or notification to the surface monitoring unit 146 for direction to appropriate entities if any problem arises during such calibration activities. Example entities may include international or national oil companies, maintenance personnel, field service operators, production engineers, and equipment owners. In order for the calibration process to proceed, a flange of the incoming flow line 102 leading to the fluid collection chamber 106 is opened, the incoming and outgoing flow lines 102, 104 are emptied and depressurized, the fluid collection and sampling chambers 106, 108 are automatically flushed and cleaned, and radiation emitted by the radioactive source 136 is measured at the detector 138 as a reference point.

An example aspect of the auto-calibration process that may be carried out includes liquid referencing to ensure accurate determination of the liquid fractions during operation of the MPFM 100. During liquid referencing, the fluid flow 101 is delivered to the MPFM 100 through the incoming flow line 102, and the fluid flow 101 is sampled automatically within the sampling chamber 108. An important aspect of the fluid flow 101 in this case is determining the water cut via the centrifuge 130, with subsequent updating of water and oil properties and mass attenuation parameters of the fluid flow 101 at the control module 116.

Once the MPFM 100 has been calibrated, the MPFM 100 can perform a comprehensive, real-time test validation process to ensure that the measured parameters and the output parameters are within an acceptable range prior to fully commissioning the MPFM 100 for operation at the well 103. Such actions may be performed when using automated functionality as further discussed below and if the well that the MPFM 100 was previously commissioned upon has the same hydrocarbon effluent. For example, the fluid flow 101 is delivered to the fluid collection chamber 106, and the fluid flow 101 is sampled automatically within the sampling chamber 108. The fluid processing devices 112 may then send signals corresponding to measured parameters to the surface monitoring unit 146 in real time. The measured parameters are then tested and verified on-site against physical sampling (for example, manual fluid sampling by an operator) of the fluid flow 101, and the input models may be updated in case a significant deviation is identified. Frequent measurements may be initiated via the surface monitoring unit 146 or via field measurements for preventive maintenance, and troubleshooting alarms and notifications may be generated as necessary to ensure performance integrity of the MPFM 100 at all times. The output parameters may be compared to the virtual metering results or a historical performance for validating the tests in real time and proposing a corrective action (for example, maintaining the well on stream for an extended period of time to ensure rate stabilization) in case of deviations. The accuracy of the validation process may correspond with industry standards of 5% of absolute error of the water cut, 10% liquid relative error, and 15% gas relative error. Such test validation activities may be performed over a period of time that depends on the flow rate of the fluid flow 101, a pressure of the wellhead, and a temperature of the wellhead. The period of time may be anywhere from about 4 hours (h) to about 24 h, depending an operating environment and stabilization of the well 103 . . . .

Figure 4:
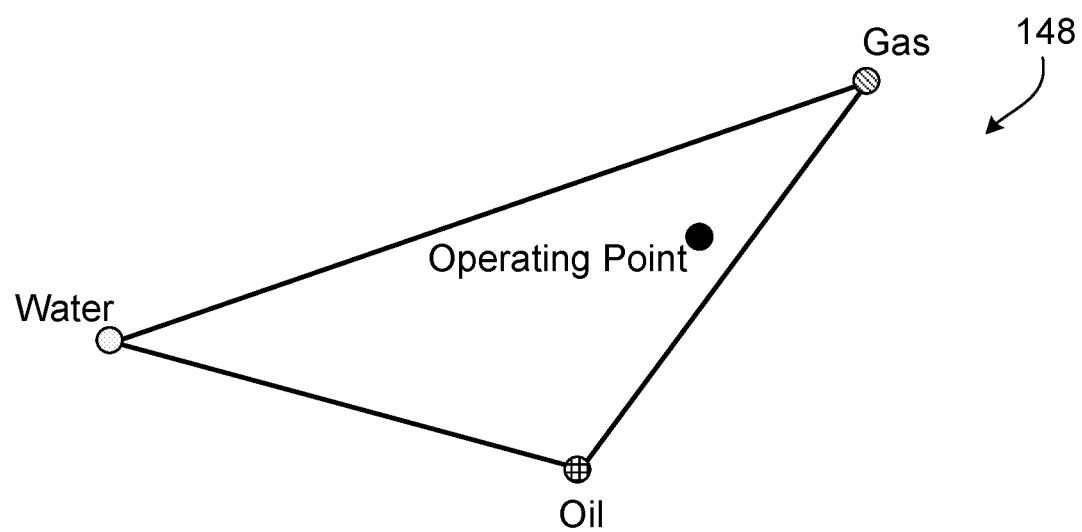
FIG. 4 is a schematic illustration of an operational envelope of the multiphase flowmeter of FIG. 1.

Regarding validity of the measured and output parameters, the MPFM 100 is normally associated with a triangular operational envelope 148, as shown in FIG. 4. Successful operation of the MPFM 100 should falls within the operational envelope 148, which extends between operational points defined alone by water, oil, and gas. In some examples, the operational envelope 148 may be set by an operator prior to full commissioning of the MPFM 100 based on a well potential, other characteristics of a well, and input ranges of densities or measurable parameters, such as water cut and temperature. During the test validation period, the control module 116 is designed to correct its output parameters before transmitting the output parameters to the surface monitoring unit 146. Such output parameters may include temperature, pressure, differential pressure, mixture density, and flow rates of each phase of the fluid flow 101, among others. Unconventional output parameters (for example, input voltage and gamma count) that support automation of alarms or notifications associated with operation of the MPFM 100 may also be corrected. Such parameters may be corrected using input data (for example, the PVT curve) if the parameters are incorrect or not up to date.

In some examples, the control module 116 may correct the output parameters using artificial intelligence and data mining with historical trending analysis. In some examples, the control module 116 may generate an alarm or notification related to a discrepancy between actual and expected output parameters. In some cases, an alarm or notification may be trigged by operational issues, such as data connectively breakouts, inadequate power to the MPFM 100, or a differential pressure at the collection tube 118 that is outside of the operating range of the MPFM 100. The alarms may be addressed by engineers to further evaluate and check historical performance as well as evaluate the need for remote or field troubleshooting visits.

As discussed above, the collection tube 118 of the MPFM 100 operates according to the principles of the Venturi effect, and the size of the intermediate channel 124 is the main component that affects accurate measurement of flow rate of the fluid flow 101. The walls 126 of the collection tube 118 are adjustable based on the flow rate of the fluid flow 101, which is important for operating at wells with various degrees of hydrocarbons, various types of American Petroleum Institute reservoir effluents, and differing well potentials. The control module 118 of the MPFM 100 uses artificial intelligence to perform data mining of a historical trending analysis of the well 103 and the well potential. Such data typically reside in a historical database or a spreadsheet template. The control module 116 can retrieve such data in a summarized format and compare the data to the output parameters of the MPFM 100 in order to identify any significant differences. Based on the flow rate of the fluid flow 101 measured in real time, the MPFM 100 can automatically change the size of the intermediate channel 124 of the collection tube 118 to correctly accommodate and measure the flow rate of the fluid flow 101. Furthermore, the input device 152 at the surface monitoring unit 148 or at another location can allow for manual control of the MPFM 100 (for example, via supervisory control and data acquisition (SCADA)) as an alternative to control of certain parameters via the control module 116.

The MPFM 100 can measure the flow rate of the fluid flow 101 with a high degree of accuracy by using accurate, real-time input data, such as the PVT profile and water salinity of the fluid flow 101 (for example, which vary based on the well). In some cases, introduction of water (for example, an instance in which a well becomes classified as wet), or a sudden, significance increase in water production would otherwise compromise the measured and output parameters without use of such updated real-time data. For example, the MPFM 100 can collect samples in the sampling chamber 106 when necessary, analyze the samples, and update the PVT profile and other related information at the control module 116. Accordingly, the MPFM 100 can determine flow rates, compare the flow rates with flow rates from previous tests, and produce a data accuracy analysis through SCADA. Such analysis is advantageously performed whenever a there is a sudden data deviation or irregularity between the current data and expected values or whenever the data points are outside of the operational envelope 148. The expected values may be values that are estimated or forecasted by virtual metering, historical performance, production logging tool (PLT) results, or an electrical submersible pump (ESP) curve with a pre-set deviation tolerance. The control module 116 can generate alarms or notifications related to any deviations and any associated corrective actions that should be taken.

The MPFM 100 can also verify whether or not a correct well profile has been inputted and that no additional fluid flows from other wells are flowing through the incoming flow line 102 into the MPFM 100 based on the real-time data. Furthermore, the MPFM 100 generate an alarm whenever the radioactive source 136 begins to perform irregularly, becomes, weak, or requires replacement, any of which statuses may cause non-compliance with the Health, Safety, Security and Environment (HSSE) standards of the industry. In contrast, conventional MPFMs are not designed to monitor the data accuracy and validity via sampling as described, send automatic notifications concerning any deviations, auto-update input parameters based on sampling, or impose soft or physical auto-corrective actions.

According to above-discussed features, the MPFM 100 is a smart, robust device that is adaptable to variable conditions of multiple wells for accurate characterization of a multiphase fluid flow. The MPFM 100 may be employed in various instances. In some implementations, the MPFM 100 may be installed on a platform in an offshore field or at a drill site in an onshore field and is adaptable to perform successfully for wells with various well potentials. For example, a vertical well typically produces at lower flow rates than horizontal or multi-lateral wells. The size of the collection tube 118 is a critical component for accurate, valid measurements of the flow rate of the fluid flow 101. Accordingly, the automatic, adjustable nature of the collection tube 110 allows the MPFM 100 to be utilized at a variety of wells.

In some examples, the MPFM 100 may be installed at a well that is newly drilled in any given platform or drill site. Such a well may have reservoir properties that are not initially consistent with a configuration of the MPFM 100. When using conventional MPFMs, a sample must be taken manually by an operator to conduct liquid referencing, and then a model must be initiated for appropriately measuring the well potential. Logistical and operational resources associated with determining such a model for attempting to appropriately account for changing fluid properties and effluent behavior can be challenging and time consuming, especially in offshore environments. However, the MPFM 100 can advantageously automate determination, implementation, and updates of such models.

Figure 5:
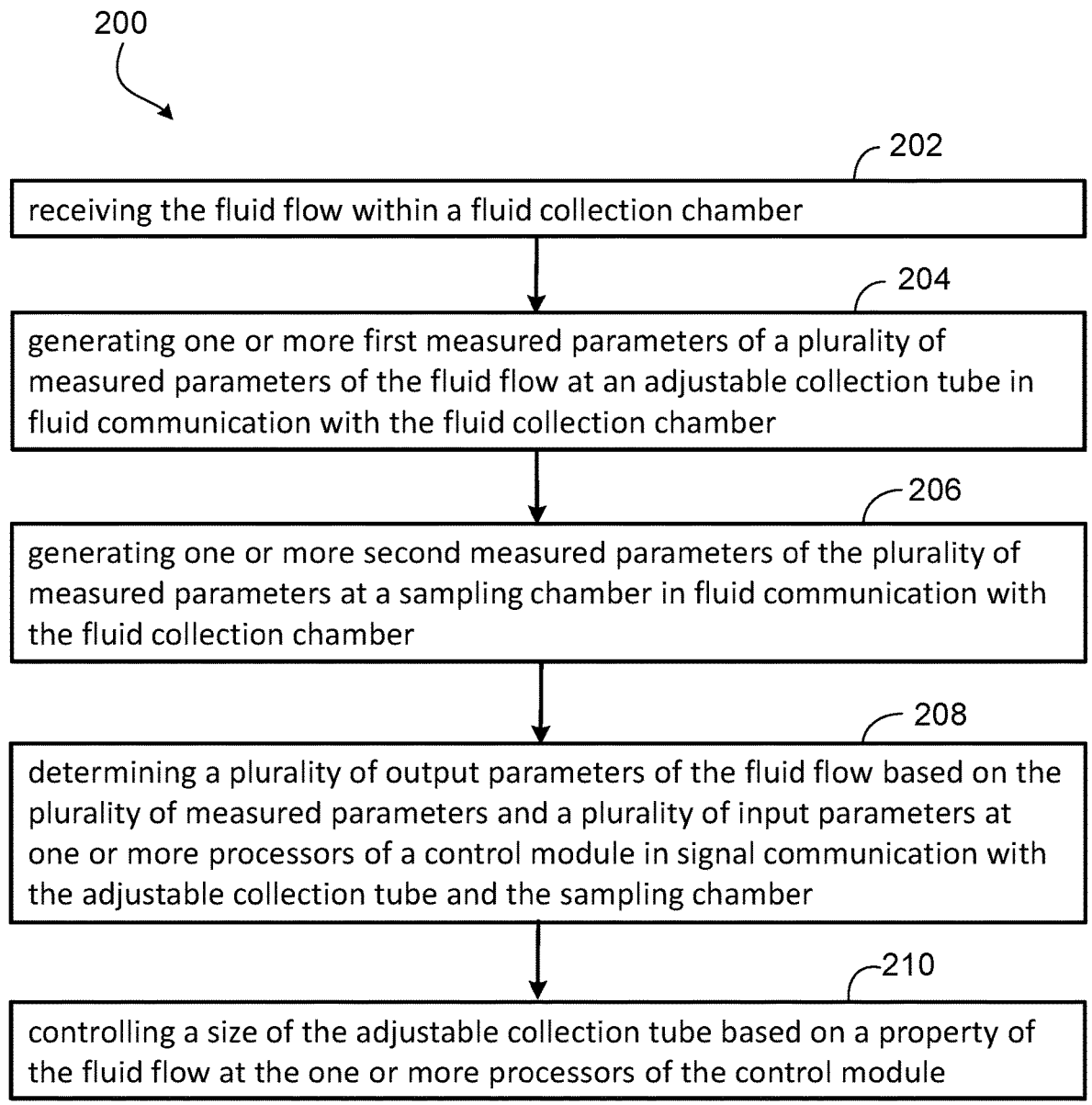
FIG. 5 is a flow chart illustrating an example method of analyzing a fluid flow produced by a well using the multiphase flowmeter of FIG. 1.

FIG. 5 is a flow chart illustrating an example method 200 of analyzing a fluid flow (for example, the fluid flow 101) produced by a well (for example, the well 103). In some embodiments, the method 200 includes a step 202 for receiving the fluid flow within a fluid collection chamber (for example, the fluid collection chamber 106). In some embodiments, the method 200 includes a step 204 for generating one or more first measured parameters of multiple measured parameters of the fluid flow at an adjustable collection tube (for example, the collection tube 118) in fluid communication with the fluid collection chamber. In some embodiments, the method 200 includes a step 206 for generating one or more second measured parameters of the multiple measured parameters at a sampling chamber (for example, the sampling chamber 108) in fluid communication with the fluid collection chamber. In some embodiments, the method 200 includes a step 208 for determining multiple output parameters of the fluid flow based on the multiple measured parameters and multiple input parameters at one or more processors (for example, the one or more processors 150) of a control module (for example, the control module 116) in signal communication with the adjustable collection tube and the sampling chamber. In some embodiments, the method 200 includes a step 210 for controlling a size of the adjustable collection tube based on a property of the fluid flow at the one or more processors of the control module.

As discussed above, the MPFM 100 provides several advantages over conventional MPFMs. The MPFM 100 produces accurate and valid measurements of well potential continuously, mitigates costs that would otherwise arise without such continuous, accurate measurements, leads to continuous utilization of equipment (for example, especially in offshore environments), prolongs the lifetime and usage of assets, reduces the need for human intervention and associated human exposure to radioactive source emission, improves adherence to HSSE standards in association with reduced field interventions, and provides regular, frequent hydrocarbon effluent samples.

While the MPFM 100 has been described and illustrated with respect to certain dimensions, sizes, shapes, arrangements, materials, and methods 200, in some embodiments, an MPFM that is otherwise substantially similar in construction and function to the MPFM 100 may include one or more different dimensions, sizes, shapes, arrangements, and materials or may be utilized according to different methods. In some embodiments, a set of selectable collection tubes 154 that are similar in construction and function to the collection tube 118 may be sized for installation into a Venturi chamber of a different size of an MPFM that must be sized down for a relatively low well potential or sized up for a relatively high well potential.

Accordingly, other embodiments are also within the scope of the following claims.

What is claimed is:

1. A flowmeter comprising:
a fluid collection chamber for receiving a fluid flow;
an adjustable collection tube configured to receive a portion of the fluid flow to generate one or more first measured parameters of a plurality of measured parameters of the fluid flow;
a sampling chamber configured to measure samples of the fluid flow to generate one or more second measured parameters of the plurality of measured parameters of the fluid flow; and
a control module in signal communication with the adjustable collection tube and the sampling chamber and comprising one or more processors by which the control module automatically performs operations comprising:
determining a plurality of output parameters of the fluid flow based on the plurality of measured parameters and a plurality of input parameters, and
controlling a size of the adjustable collection tube based on a property of the fluid flow.

2. The flowmeter of claim 1, wherein the property comprises a bulk flow rate, and wherein the operations further comprise:
causing a size of the adjustable collection tube to increase when the bulk flow rate increases; and
causing a size of the adjustable collection tube to decrease when the bulk flow rate decreases.

3. The flowmeter of claim 1, wherein the sampling chamber is configured to sample the fluid flow continuously and to send signals corresponding to the one or more second measured parameters to the control module in real time.

4. The flowmeter of claim 3 wherein the operations further comprising receiving the plurality of input parameters, the plurality of input parameters being related to the fluid flow and to a well that produces the fluid flow.

5. The flowmeter of claim 4, wherein the operations further comprise updating one or more of the plurality of input parameters based on one or more of the plurality of output parameters.

6. The flowmeter of claim 1, wherein the operations further comprise sending the plurality of output parameters to a surface monitoring unit.

7. The flowmeter of claim 1, wherein the operations further comprise generating an alarm or a notification when a difference between a value of an output parameter and an expected value exceeds a threshold value.

8. The flowmeter of claim 1, wherein the fluid flow comprises a plurality of phases, and wherein the plurality of output parameters comprise bulk properties of the fluid flow and phase properties of the plurality of phases.

9. The flowmeter of claim 1, wherein the operations further:
comprise auto-calibrating the flowmeter using one or more of the plurality of measured parameters; and
validating one or more of the plurality of output parameters based on one or more of the plurality of measured parameters.

10. The flowmeter of claim 1, further comprising one or more fluid processing devices configured to measure parameters of the fluid flow.

11. A method of analyzing a fluid flow produced by a well, the method comprising:
receiving the fluid flow within a fluid collection chamber;
generating one or more first measured parameters of a plurality of measured parameters of the fluid flow at an adjustable collection tube in fluid communication with the fluid collection chamber;
generating one or more second measured parameters of the plurality of measured parameters at a sampling chamber in fluid communication with the fluid collection chamber;
determining a plurality of output parameters of the fluid flow based on the plurality of measured parameters and a plurality of input parameters at one or more processors of a control module in signal communication with the adjustable collection tube and the sampling chamber; and
controlling a size of the adjustable collection tube based on a property of the fluid flow at the one or more processors of the control module.

12. The method of claim 11, wherein the property comprises a bulk flow rate, and method further comprises:
increasing a size of the adjustable collection tube when the bulk flow rate increases; and
decreasing the size of the adjustable collection tube when the bulk flow rate decreases.

13. The method of claim 11, wherein the sampling chamber is configured to sample the fluid flow continuously and to send signals corresponding to the one or more second measured parameters to the control module in real time.

14. The method of claim 13, further comprising receiving the plurality of input parameters at the control module, the plurality of input parameters being related to the fluid flow and to the well.

15. The method of claim 14, further comprising updating one or more of the plurality of input parameters based on one or more of the plurality of output parameters at the control module.

16. The method of claim 11, further comprising sending the plurality of output parameters from the control module to a surface monitoring unit.

17. The method of claim 11, further comprising generating an alarm or a notification when a difference between a value of an output parameter and an expected value exceeds a threshold value at the control module.

18. The method of claim 11, wherein the fluid flow comprises a plurality of phases, and wherein the plurality of output parameters comprise bulk properties of the fluid flow and phase properties of the plurality of phases.

19. The method of claim 11, further comprising:
   comprise auto-calibrating the flowmeter at the control module using one or more of the plurality of measured parameters; and
   validating one or more of the plurality of output parameters at the control module based on one or more of the plurality of measured parameters.

20. The method of claim 11, further comprising generating one or more third measured parameters of the plurality of measured parameters at one or more fluid processing devices in fluid communication with the fluid collection chamber.

\* \* \* \* \*